United States Patent [19]

Boller et al.

[11] 4,309,539
[45] * Jan. 5, 1982

[54] PYRIMIDINE DERIVATIVES

[75] Inventors: Arthur Boller, Binningen; Marco Cereghetti, Basel; Hanspeter Scherrer, Therwil, all of Switzerland

[73] Assignee: Hoffmann-La Roche Inc., Nutley, N.J.

[*] Notice: The portion of the term of this patent subsequent to Dec. 13, 1994, has been disclaimed.

[21] Appl. No.: 101,604

[22] Filed: Dec. 10, 1979

Related U.S. Application Data

[63] Continuation of Ser. No. 885,724, Mar. 13, 1978, abandoned.

[51] Int. Cl.$^3$ ............................................. C07D 239/20
[52] U.S. Cl. .................................. 544/242; 544/335; 252/299.1
[58] Field of Search .................... 544/242, 335, 333

[56] References Cited

U.S. PATENT DOCUMENTS 3,997,536  12/1976  Boller et al. .................... 544/242
4,062,798  12/1977  Boller et al. .................... 544/335

*Primary Examiner*—Nicholas S. Rizzo
*Attorney, Agent, or Firm*—Jon S. Saxe; George M. Gould; Peter R. Shearer

[57] ABSTRACT

Optically active pyrimidines of the formula

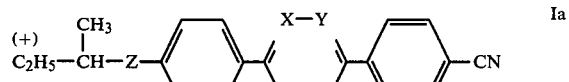

and

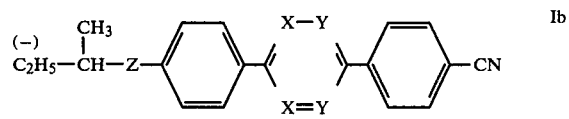

wherein Z is $-(CH_2)_n-$ or $-(CH_2)_n-O-$ wherein n is an integer of 1 to 4 and each of the symbols X is a nitrogen atom and each of the symbols Y is $-CH-$ or each of the symbols Y is a nitrogen atom and each of the symbols X is $-CH-$, useful for electro-optical purposes, as well as liquid crystalline mixtures for electro-optical purposes containing compounds of the formula Ia and/or Ib, are described.

The compounds of formulas Ia and Ib are useful for electro-optical purposes, for example, in electro-optical apparatuses.

17 Claims, No Drawings

PYRIMIDINE DERIVATIVES

This is a continuation of application Ser. No. 885,724, filed Mar. 13, 1978, now abandoned.

BRIEF SUMMARY OF THE INVENTION

The invention relates to optically active pyrimidine derivatives characterized by the formula

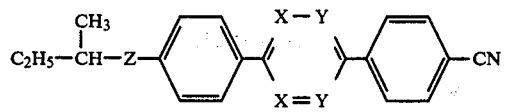

wherein Z is —(CH$_2$)$_n$— or —(CH$_2$)$_n$—O— wherein n is an integer of 1 to 4 and each of the symbols X is a nitrogen atom and each of the symbols Y is —CH— or each of the symbols Y is a nitrogen atom and each of the symbols X is —CH—.

In another aspect, the invention relates to liquid crystalline mixtures for electrooptical purposes containing one or more optically active compounds of formula I.

DETAILED DESCRIPTION OF THE INVENTION

The optically active pyrimidine derivatives of the invention are characterized by the formula

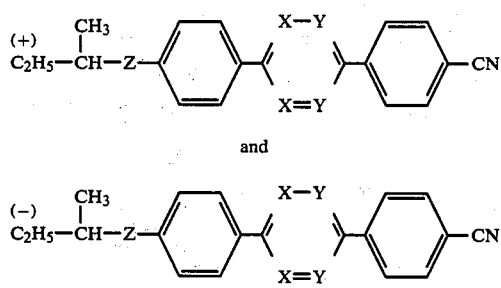

wherein Z is —(CH$_2$)$_n$— or —(CH$_2$)$_n$—O— wherein n is an integer of 1 to 4 and each of the symbols X is a nitrogen atom and each of the symbols Y is —CH— or each of the symbols Y is a nitrogen atom and each of the symbols X is —CH—.

It is known that the addition of cholesteric compounds to a matrix of nematic liquid crystals with positive anisotropy of the dielectric constants results in a cholesteric mixture which undergoes a cholesteric-nematic transition upon application of an electrical field. This phase transition is reversible and makes possible high switching speeds of electro-optical apparatuses operated with such mixtures. Hitherto known cholesteric compounds have had the disadvantage of usually having only very narrow mesophase range and, as a rule, a low or even a monotropic clearing point.

Surprisingly, it has now been found that the optically active pyrimidine derivatives of formula I possess not only a wide mesophase range but also a high clearing point. By means of optically active pyrimidine derivatives of formula I, such properties in the corresponding mixtures can also be improved drastically. Moreover, the optically active pyrimidine derivatives of formula I possess a strong positive anisotropy of the dielectric constants, which has a further favorable influence on the positive anisotropy of the dielectric constants of corresponding mixtures. Also, the optically active pyrimidine derivatives of the invention have a high chemical stability.

The mixture which contain the optically active pyrimidine derivatives of formula I can also contain pleochroitic coloring substances.

Exemplary of the optically active pyrimidine derivatives of formula I are:
5-[4'-(+)-2''-Methyl-1'''-butylphenyl]-2-(4-cyanophenyl)-pyrimidine,
5-[4'-(+)-3''-methyl-1'''-pentylphenyl]-2-(4-cyanophenyl)-pyrimidine,
5-[4'-(+)-4''-methyl-1'''-hexylphenyl]-2-(4-cyanophenyl)-pyrimidine,
5-[4'-(+)-5''-methyl-1'''-heptylphenyl]-2-(4-cyanophenyl)-pyrimidine,
5-[4'-(+)-2''-methyl-1'''-butyloxyphenyl]-2-(4-cyanophenyl)-pyrimidine,
5-[4'-(+)-3''-methyl-1'''-pentyloxyphenyl]-2-(4-cyanophenyl)-pyrimidine,
5-[4'-(+)-4''-methyl-1'''-hexyloxyphenyl]-2-(4-cyanophenyl)-pyrimidine,
5-[4'-(+)-5''-methyl-1'''-heptyloxyphenyl]-2-(4-cyanophenyl)-pyrimidine,
2-[4'-(+)-2''-methyl-1'''-butylphenyl]-5-(4-cyanophenyl)-pyrimidine,
2-[4'-(+)-3''-methyl-1'''-pentylphenyl]-5-(4-cyanophenyl)-pyrimidine,
2-[4'-(+)-4''-methyl-1'''-hexylphenyl]-5-(4-cyanophenyl)-pyrimidine,
2-[4'-(+)-5''-methyl-1'''-heptylphenyl]-5-(4-cyanophenyl)-pyrimidine,
2-[4'-(+)-2''-methyl-1'''-butyloxyphenyl]-5-(4-cyanophenyl)-pyrimidine,
2-[4'-(+)-3''-methyl-1'''-pentyloxyphenyl]-5-(4-cyanophenyl)-pyrimidine,
2-[4'-(+)-4''-methyl-1'''-hexyloxyphenyl]-5-(4-cyanophenyl)-pyrimidine,
2-[4'-(+)-5''-methyl-1'''-heptyloxyphenyl]-5-(4-cyanophenyl)-pyrimidine
and their (—) optical antipodes. Especially preferred optically active pyrimidine derivatives of this invention are those in which each of X is —CH— and each of Y is nitrogen.

The optically active pyrimidine derivatives of formula I can be prepared as follows:

(a) reacting a compound of the formula

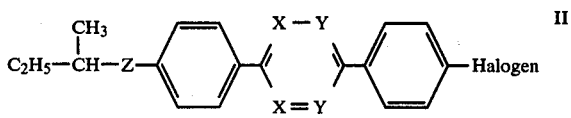

wherein X, Y and Z are as previously described, with copper-(I) cyanide, sodium cyanide or potassium cyanide, or (b) for the preparation of optically active pyrimidine derivatives of formula I wherein each of the symbols X is —CH— and each of the symbols Y is nitrogen, by dehydrating a compound of the formula

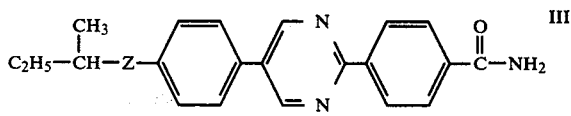

wherein Z is as previously described,
or (c) for the preparation of optically active pyrimidine derivatives of formula I wherein each of the symbols X is nitrogen and each of the symbols Y is —CH—, by dehydrating a compound of the formula

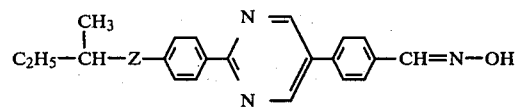   IV wherein Z is as previously described,
the starting materials of formulas II, III and IV can be used in the optically active or racemic form. When a racemic starting material of formula II, III or IV is used, a resulting racemate is separated into its optical antipodes.

In process embodiment (a), a compound of formula II is reacted with copper-(I) cyanide, sodium cyanide or potassium cyanide. This reaction is conveniently carried out in an inert organic solvent, such as ethyleneglycol, tetrahydrofuran, dimethylformamide, dimethylsulfoxide, pyridine, acetonitrile, or the like. The temperature and pressure of the reaction are not critical aspects of the reaction. The reaction is conveniently carried out at atmospheric pressure and a temperature in the range of room temperature and the boiling point of the reaction mixture. If a halogen atom is present in the compound of formula II, it is preferably bromine.

The dehydration of a compound of formula III in accordance with process embodiment (b) can be carried out utilizing any suitable dehydrating agent, such as phosphorus oxychloride, phosphorus pentoxide, thionyl chloride, acetic anhydride or the like. The dehydration can be carried out in an inert organic solvent, for example, a hydrocarbon or halogenated hydrocarbon or the like, if necessary, in the presence of a base such as sodium acetate, pyridine, triethanolamine or the like. The dehydration can, however, also be carried out in the absence of an organic solvent. The dehydration is conveniently carried out at the reflux temperature of the mixture. Although the pressure is not critical, the dehydration is preferably carried out at atmospheric pressure.

In process embodiment (c), a compound of formula IV is dehydrated. The dehydration is conveniently carried out utilizing acetic anhydride or utilizing anhydrous sodium acetate in glacial acetic acid or also under the conditions described hereinbefore in connection with the dehydration of a compound of formula III. The dehydration is carried out a the reflux temperature of the reaction mixture. Although the pressure is not critical, the dehydration is advantageously carried out at atmospheric pressure.

The cleavage of an obtained racemate into its optical antipodes can be carried out in a known manner, for example, by salt formation with an optically active acid or, after saponification of the cyano group, by salt formation with an optically active base and fractional crystallization of the resulting salts.

The compounds of formulas II, III and IV which are used as the starting materials are novel and also form part of the present invention.

The novel compounds of formulas II, III and IV can be prepared in a known manner, as illustrated by Formula Schemes I to IV hereinafter for compounds wherein the halogen atom is bromine and the symbol A is a group of the formula

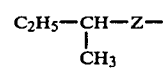

wherein Z is as previously described.

Formula Scheme I

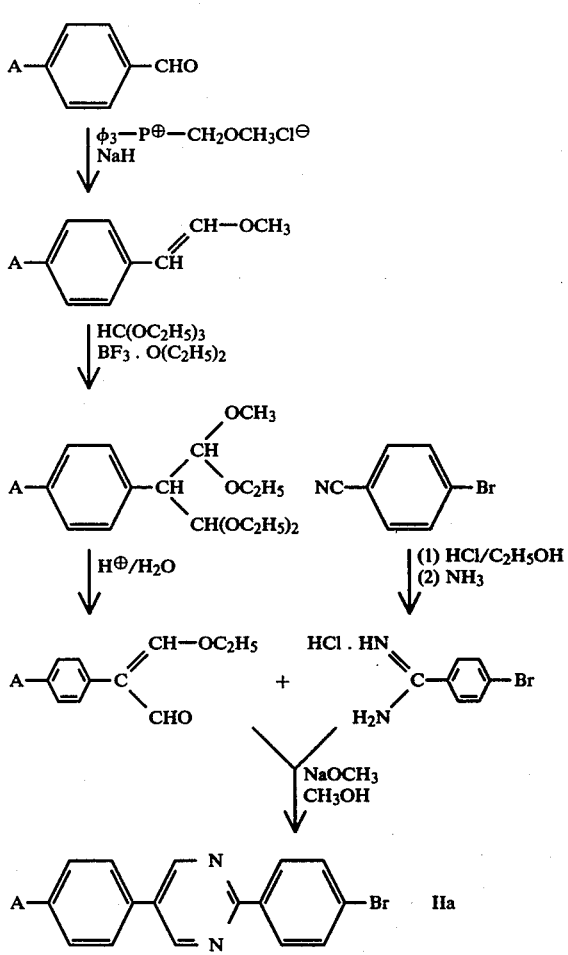

Formula Scheme II

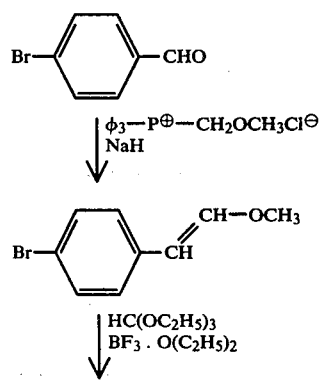

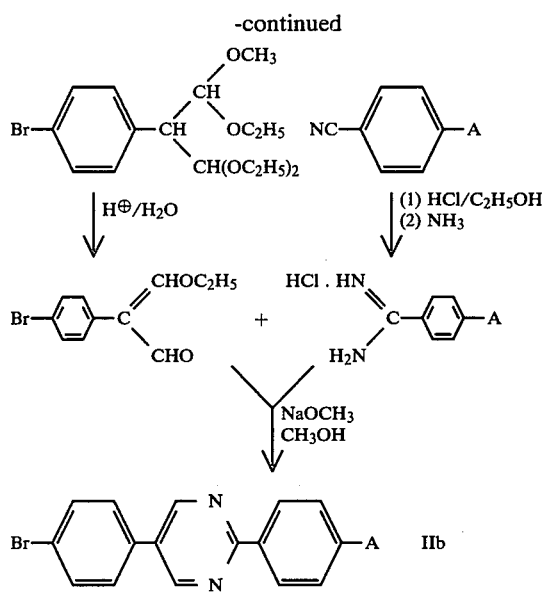
Formula Scheme III
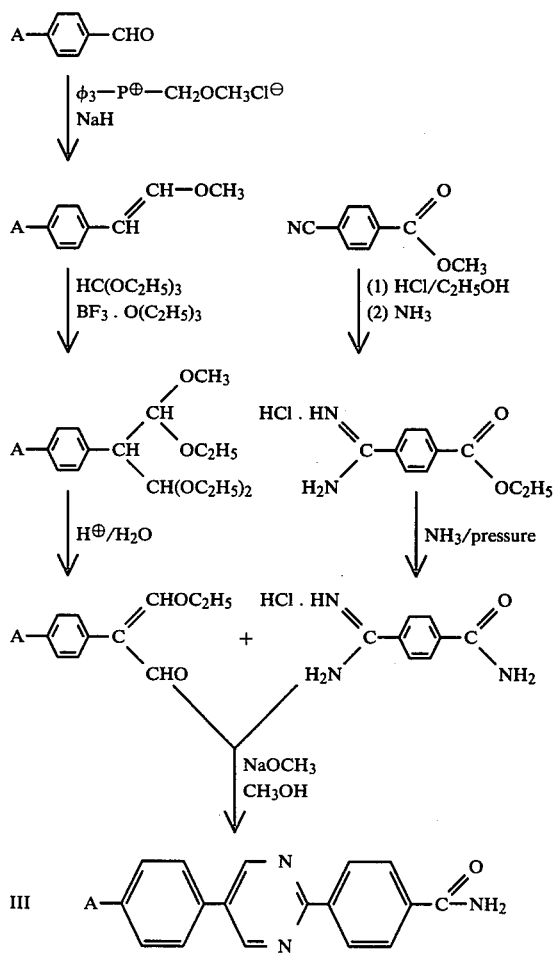
Formula Scheme IV
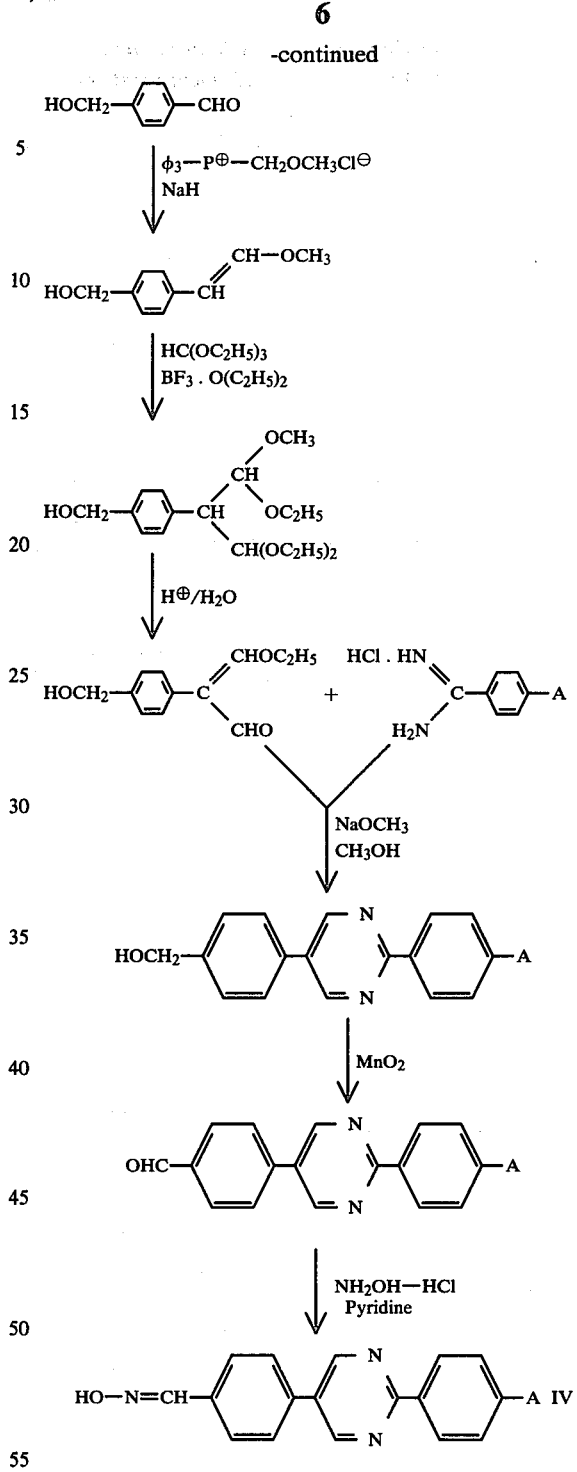
The optically active pyrimidine derivatives of formula I are conveniently utilized in the form of mixtures with nematic substances; for example, with compounds of the formula
wherein $R_6$ is straight-chain alkyl containing 2 to 8 carbon atoms, straight-chain alkoxy containing 4 to 7 carbon atoms, straight-chain alkanoyloxy containing 2 to 8 carbon atoms or straight-chain alkylcarbonate containing 2 to 11 carbon atoms,
and/or with compounds of the formula

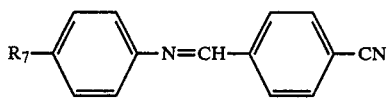

VI wherein $R_7$ is straight-chain alkyl containing 4 to 7 carbon atoms or straight-chain alkylcarbonate containing 2 to 11 carbon atoms,
and/or with compounds of the formula

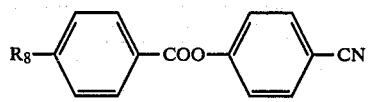

VII wherein $R_8$ is straight-chain alkyl containing 4 to 8 carbon atoms, straight-chain alkoxy containing 5 to 8 carbon atoms, straight-chain alkanoyloxy containing 2 to 8 carbon atoms or straight-chain alkylcarbonate containing 3 to 11 carbon atoms,
and/or with compounds of the formula

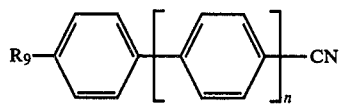

VIII wherein $R_9$ is straight-chain alkyl containing 4 to 8 carbon atoms, straight-chain alkoxy containing 4 to 8 carbon atoms, straight-chain alkanoyloxy containing 4 to 9 carbon atoms or straight-chain alkylcarbonate containing 4 to 11 carbon atoms and n is 1 or 2,
and/or with trans-cinnamic acid esters of the formula

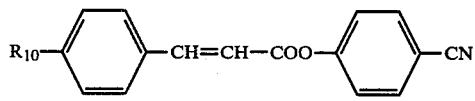

IX wherein $R_{10}$ is straight-chain alkyl containing 1 to 8 carbon atoms,
and/or with compounds of the formula

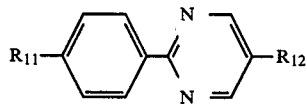

X wherein one of $R_{11}$ and $R_{12}$ is cyano and the other is straight-chain alkyl containing 3 to 9 carbon atoms, straight-chain alkoxy containing 2 to 9 carbon atoms or straight-chain alkanoyloxy containing 2 to 9 carbon atoms,
and/or with compounds of the formula

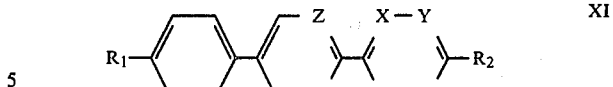

XI wherein each of the symbols X is nitrogen and each of the symbols Y and Z is —CH—, or each of the symbols Y is nitrogen and each of the symbols Y and Z is —CH—, or each of the symbols Z is nitrogen and each of the symbols X and Y is —CH—, and one of $R_1$ and $R_2$ is cyano and the other is straight-chain alkyl containing 1 to 7 carbon atoms, straight-chain alkoxy containing 1 to 7 carbon atoms or straight-chain alkanoyloxy containing 2 to 7 carbon atoms.

The optically active pyrimidine derivatives of formula I are utilized in nematic mixtures for electro-optical purposes in a weight ratio which preferably corresponds to the eutectic composition. The amount of an optically active pyrimidine derivative of formula I present in a nematic mixture is, however, generally in the range of from about 1 to about 40 percent by weight, preferably in the range of from about 5 to about 30 percent by weight and most preferably in the range of from about 5 to about 15 percent by weight.

Examples of preferred mixtures, with percentages expressed as mol percentages, are the following:

12.7% of p-[(p-n-propylbenzyliden)amino]benzonitrile, 34.5% of p-[(p-butylbenzyliden)amino]benzonitrile, 46.9% of p-[(p-hexylbenzyliden)amino]benzonitrile and 5.4% of 5-[4'-(+)-2'''-methyl-1''-butyloxyphenyl]-2-(4-cyanophenyl)-pyrimidine; clearing point 72.2° C.;

11.2% of p-n-butylbenzoic acid p'-cyanophenyl ester, 12.5% of p-n-pentylbenzoic acid p'-cyanophenyl ester, 16.0% of p-n-hexylbenzoic acid p'-cyanophenyl ester, 17.2% of p-n-heptylbenzoic acid p'-cyanophenyl ester, 11.9% of 5-n-pentyl-2-(4-cyanophenyl)-pyrimidine, 23.2% of 5-n-heptyl-2-(4-cyanophenyl)-pyrimidine and 7.3% of 5-[4'-(+)-2'''-methyl-1''-butyloxyphenyl]-2-(4-cyanophenyl)-pyrimidine; clearing point 65.6° C.; and 55.7% of 4-pentyl-4'-cyanobiphenyl, 33.2% of 4-pentyloxy-4'-cyanobiphenyl and 6.4% of 5-[4'-(+)-2'''-methyl-1''-butyloxphenyl]-2-(4-cyanophenyl)-pyrimidine; clearing point 60.3° C.

The compounds of formula XI hereinbefore are novel and can be obtained, for example, by reacting a compound of the formula

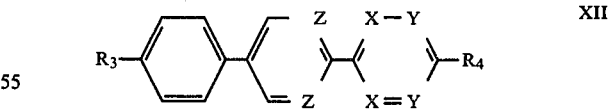

XII wherein one of $R_3$ and $R_4$ is straight-chain alkyl containing 1 to 7 carbon atoms, straight-chain alkoxy containing 1 to 7 carbon atoms or straight-chain alkanoyloxy containing 2 to 7 carbon atoms and the other is halogen, and X, Y and Z are as previously described,
with copper-(I) cyanide, sodium cyanide or potassium cyanide.

This reaction can be carried out in an analogous manner to that described earlier in connection with the reaction of a compound of formula II with copper-(I) cyanide, sodium cyanide or potassium cyanide.

The preparation of the compounds of formula XII can be carried out according to the disclosure in German Patent Publication (DOS) No. 2,641,724 and is illustrated in Formula Schemes A to F which follow for compounds wherein one of $R_3$ and $R_4$ is straight-chain alkyl containing 1 to 7 carbon atoms and the other is bromine.

Formula Scheme A

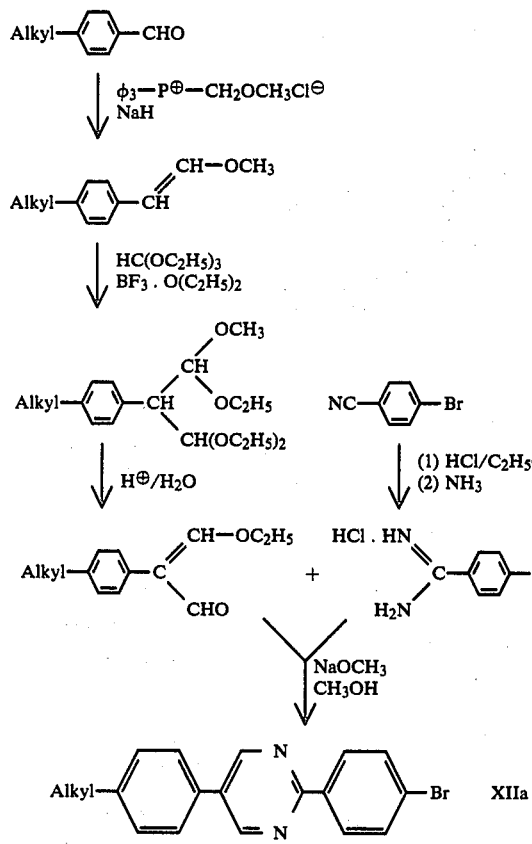

Formula Scheme B

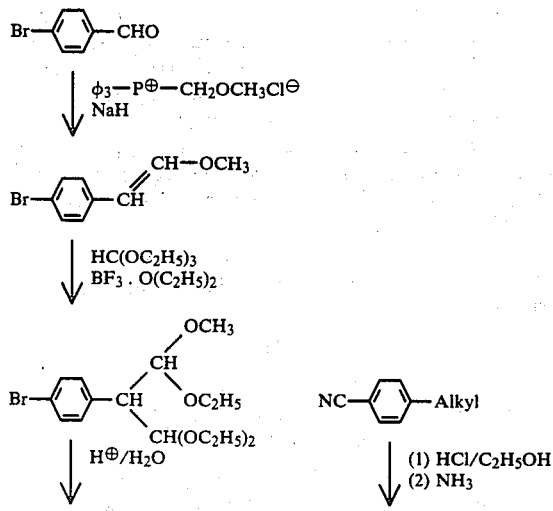

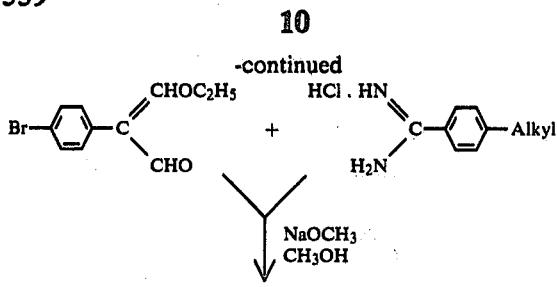

Formula Scheme C

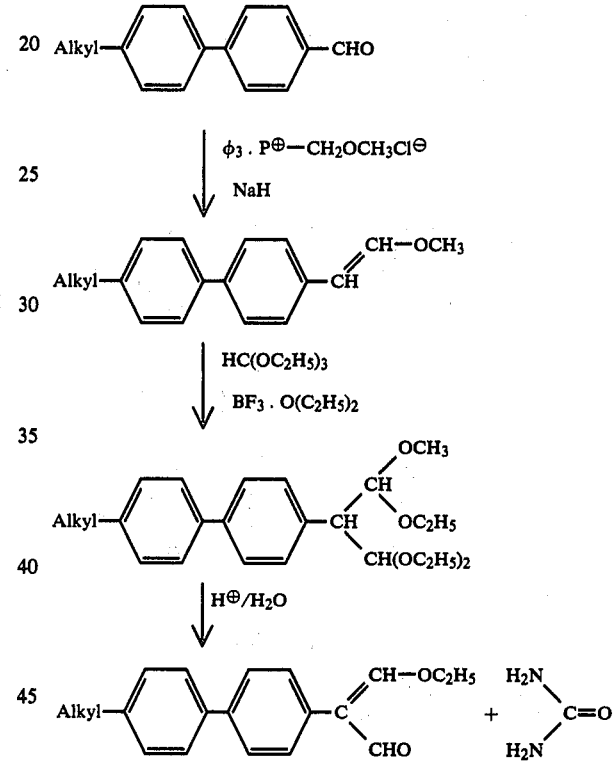

XIIc

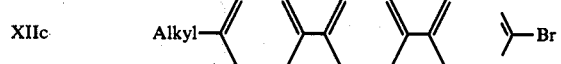

Formula Scheme D

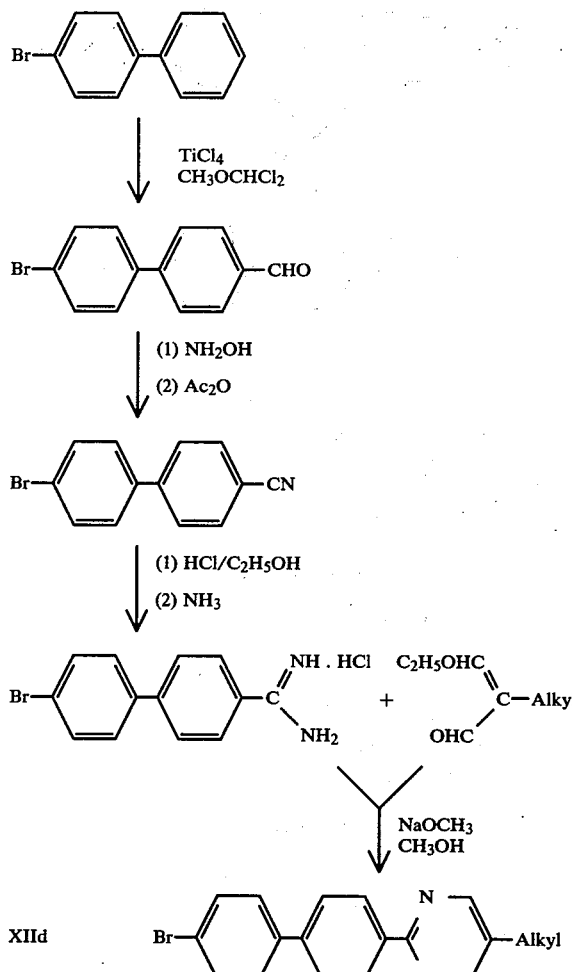

Formula Scheme E

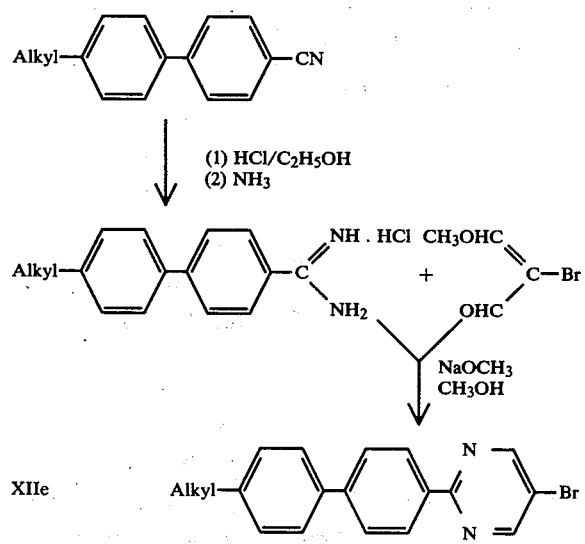

Formula Scheme F

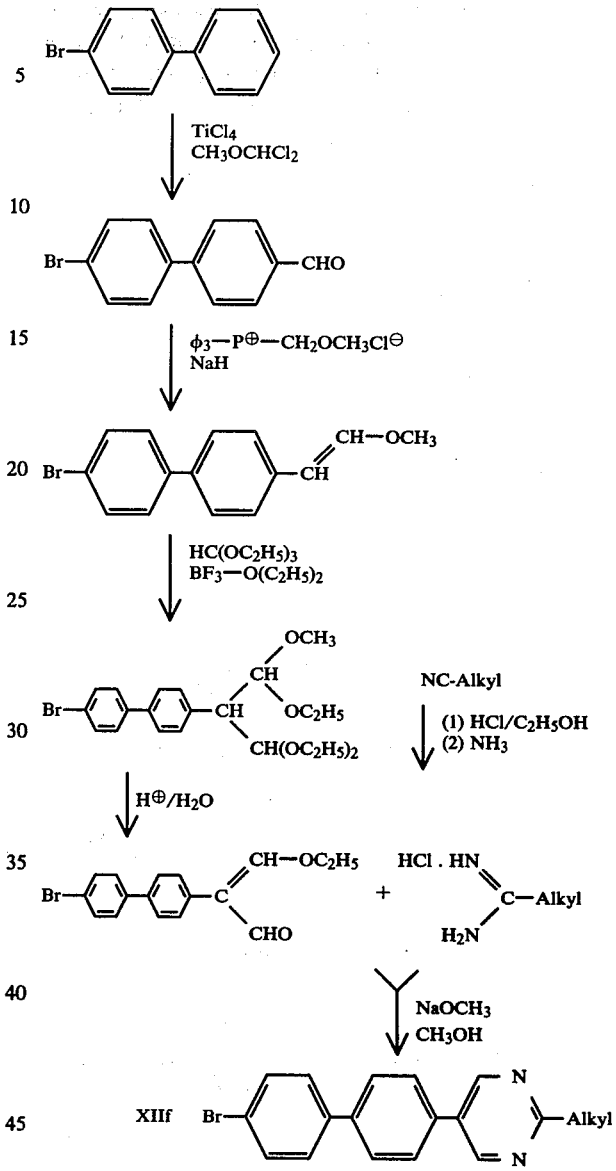

The term "straight-chain alkyl containing 1 to 7 carbon atoms", as used in this specification, denotes methyl, ethyl, n-propyl, n-butyl, n-pentyl, n-hexyl and n-heptyl. The term "straight-chain alkoxy containing 1 to 7 carbon atoms" denotes methoxy, ethoxy, n-propoxy, n-butoxy, n-pentyloxy, n-hexyloxy and n-heptyloxy. The term "straight-chain alkanoyloxy containing 2 to 7 carbon atoms" denotes acetoxy, n-propionyloxy, n-butyryloxy, n-valeryloxy, n-hexanoyloxy and n-heptanoyloxy.

The following Examples further illustrate the invention. All temperatures are in degrees Centigrade, unless otherwise mentioned.

EXAMPLE 1

Preparation of 2-[4'-(+)-2''-methyl-1''-butylphenyl]-5-(4-cyanophenyl)-pyrimidine 1.9 G. of 2-[4'-(+)-2''-methyl-1''-butylphenyl]-5-(4-bromophenyl)-pyrimidine are heated at reflux for 21 hours in 50 ml. of dimethylformamide with 2.5 g. of copper-(I) cyanide (content 70%). After cooling, the mixture is stirred up with 25 ml. of 10% aqueous ethylenediamine solution and subsequently extracted with methylene chloride. The extract is again washed with aqueous ethylenediamine solution and then several times with water until neutral. The crude product obtained after evaporation is chromatographed on 150 g. of silica gel with toluene/1% acetone. There are obtained firstly traces of starting material and then fractions containing pure 2-[4'-(+)-2''-methyl-1'''-butylphenyl]-5-(4-cyanophenyl)-pyrimidine.

The starting material can be prepared as follows:

A solution of 15 g. of 1-(4-bromophenyl)-2-methoxyethylene in 150 ml. of ethyl orthoformate is added dropwise at 0°–5° C. to 5 g. of boron trifluoride etherate in 200 ml. of ethyl orthoformate. The mixture is stirred overnight, the mixture reaching room temperature. The mixture is diluted with ether and washed with soda solution and then with water until neutral. The crude product obtained after evaporation yields, after recrystallization from hexane, 4-bromophenol-malonic tetraacetal.

In order to partially hydrolyze the foregoing tetraacetal, 4.5 g. thereof are dissolved in 10 ml. of ethanol, treated with 0.5 ml. of water and 1 drop of concentrated sulfuric acid, stirred overnight at 50° C. and then worked-up in the usual manner. There is thus obtained crude 2-(4-bromophenyl)-3-ethoxyacrolein which is used in the next step in crude form.

To a sodium methylate solution prepared from 0.7 g. of sodium in 25 ml. of methanol are added firstly 2.5 g. of crude 2-(4-bromophenyl)-3-ethoxyacrolein in 20 ml. of methanol and then 2.4 g. of 4-(+)-2'-methyl-1'-butyl-benzamidine hydrochloride. The mixture is heated at reflux overnight. Subsequently, the solvent is distilled off partially, the residue is treated with water and acidified with dilute hydrochloric acid. The precipitate is filtered off, washed thoroughly with water and ether and dried. The crude 2-[4'-(+)-2''-methyl-1''-butylphenyl]-5-(4-bromophenyl)-pyrimidine is used in the process without further purification.

The following compounds can be prepared in an analogous manner:

5-[4'-(+)-2''-methyl-1''-butylpheny]-2-(4-cyanophenyl)-pyrimidine, mp. 105.6°, c.p. 206.7°, $\alpha_{546} = +13.0°$, 5-[4'-(+)-3''-methyl-1''-pentylphenyl]-2-(4-cyanophenyl)-pyrimidine, 5-[4'-(+)-4''-methyl-1''-hexylphenyl]-2-(4-cyanophenyl)-pyrimidine, 5-[4'-(+)-5''-methyl-1''-heptylphenyl]-2-(4-cyanophenyl)-pyrimidine, 5-[4'-(+)-2''-methyl-1''-butyloxyphenyl]-2-(4-cyanophenyl)-pyrimidine, 5-[4'-(+)-2''-methyl-1''-butyloxyphenyl]-2-(4-cyanophenyl)-pyrimidine, mp. 150.7°, cp. 233.8°, $\alpha_{546} = +11.2°$, 5-[4'-(+)-3''-methyl-1''-pentyloxyphenyl]-2-(4-cyanophenyl)-pyrimidine, mp. 95.0°, cp. 235.7°, $\alpha_{546} = +6.6°$, 5-[4'-(+)-4''-methyl-1''-hexyloxyphenyl]-2-(4-cyanophenyl)-pyrimidine, having a melting point of 121°–122° C. and clearing point 238.5° C., $\alpha_{546} + 6.8°$, 5-[4'-(+)-5''-methyl-1''-heptyloxyphenyl]-2-(4-cyanophenyl)-pyrimidine, 2-[4'-(+)-3''-methyl-1''-pentylphenyl]-5-(4-cyanophenyl)-pyrimidine, 2-[4'-(+)-4''-methyl-1''-hexylphenyl]-5-(4-cyanophenyl)-pyrimidine, 2-[4'-(+)-5''-methyl-1''-heptylphenyl]-5-(4-cyanophenyl)-pyrimidine, 2-[4'-(+)-2''-methyl-1''-butyloxyphenyl]-5-(4-cyanophenyl)-pyrimidine, 2-[4'-(+)-3''-methyl-1''-pentyloxyphenyl]-5-(4-cyanophenyl)-pyrimidine, 2-[4'-(+)-4''-methyl-1''-hexyloxyphenyl]-5-(4-cyanophenyl)-pyrimidine, and 2-[4'-(+)-5''-methyl-1''-heptyloxyphenyl]-5-(4-cyanophenyl)-pyrimidine.

EXAMPLE 2

Preparation of 5-[4'-(+)-2''-methyl-1''-butyloxyphenyl]-2-(4-cyanophenyl)-pyrimidine 4.2 G. of 4-{5-[4'-(+)-2''-methyl-1''-butyloxyphenyl]-2-pyrimidyl}-benzoic acid amide are left at reflux for 1 hour while stirring in a mixture of 200 ml. of ethylene chloride and 2.5 ml. of phosphorus oxychloride. The mixture, diluted with ether, is washed with 2-N sodium hydroxide and then neutral with water. The organic phase is dried over sodium sulfate and evaporated to give 5-[4'-(+)-2''-methyl-1''-butyloxyphenyl]2-(4-cyanophenyl)-pyrimidine which is filtered through a short silica gel column and subsequently recrystallized from methylene chloride/methanol; melting point 149.9° C.; clearing point 233.8° C.

The starting material can be prepared as follows:

Dry hydrochloric acid gas is passed while stirring at 0° C. for 3 hours into a solution of 88.6 g. of methyl 4-cyanobenzoate in 190 ml. of benzene and 70 ml. of methanol. The mixture is left to stand at 5° C. for 5 days and the separated imidoether is then filtered off. 178 G. of this crude imidoether are suspended in 300 ml. of methanol and the suspension is cooled to about −40° C., treated with 130 g. of liquid ammonia and shaken at 70° C. for 24 hours in an autoclave. After cooling the mixture to room temperature and discharging the ammonia, the crystallized-out product is filtered off under suction, the crystals are washed with hexane and dried overnight at 50° C. in a water-jet vacuum, there being obtained 4-amidinobenzoic acid amide hydrochloride.

46.07 G. of 1-[4'-(+)-2''-methyl-1''-butyloxyphenyl]-2-methoxyethylene are added dropwise to a solution, cooled in an ice-bath, of 2 ml. of boron trifluoride ethereate in 500 ml. of ethyl orthoformate, and the mixture is subsequently stirred at room temperature. After dilution with ether, extraction and 1-N sodium hydroxide and water, drying over sodium sulfate and evaporation of the organic phase, there is obtained 4-(+)-2'-methyl-1'-butyloxyphenyl-malonic tetraacetal.

7.33 G. of 4-(+)-2'-methyl-1'-butyloxyphenyl-malonic tetraacetal are stirred overnight at 50° C. under nitrogen in 20 ml. of ethanol with 0.72 ml. of water and 2 drops of concentrated sulfuric acid. The mixture is diluted with ether and shaken out with aqueous sodium carbonate solution to separate the acidic (+)-2-methyl-butyloxyphenyl-malonaldehyde, which results as a by-product, from neutral 2-[4-(+)-2'-methyl-1'-butyloxyphenyl]-3-ethoxyacrolein.

4.46 G. of 2-[4-(+)-2'-methyl-1'-butyloxyphenyl]-3-ethoxyacrolein, 3.63 g. of the aforementioned 4-amidinobenzoic acid amide hydrochloride and 0.0254 mol. of sodium methylate (obtained by dissolving 0.584 g. of sodium metal in methanol) are suspended in 250 ml. of methanol and stirred overnight at room temperature under nitrogen. The yellow suspension is subsequently filtered under suction, washed with a small amount of ethanol and, for further purification, suspended in 1.4 liters of ether. The suspension is washed with water and again filtered. There is obtained difficultly soluble 4-{5-[4'-(+)-2"-methyl-1"-butyloxyphenyl]-2-pyrimidinyl}-benzoic acid amide.

The following optically active pyrimidine derivatives can be prepared in an analogous manner:

5-[4'-(+)-2"-methyl-1"-butylphenyl]-2-(4-cyanophenyl)-pyrimidine, mp. 105.6°, cp. 206.7°,
5-[4'-(+)-3"-methyl-1"-pentylphenyl]-2-(4-cyanophenyl)-pyrimidine,
5-[4'-(+)-4"-methyl-1"-hexylphenyl]-2-(4-cyanophenyl)-pyrimidine,
5-[4'-(+)-5"-methyl-1"-heptylphenyl]-2-(4-cyanophenyl)-pyrimidine,
5-[4'-(+)-2"-methyl-1"-butyloxyphenyl]-2-(4-cyanophenyl)-pyrimidine mp. 150.7°, cp. 233.8°,
5-[4'-(+)-3"-methyl-1"-pentyloxyphenyl]-2-(4-cyanophenyl)-pyrimidine, mp. 95.0°, cp. 235.7°,
5-[4'-(+)-4"-methyl-1"-hexyloxyphenyl]-2-(4-cyanophenyl)-pyrimidine, having a melting point of 121°–122° C. and clearing point of 238.5° C. and
5-[4'-(+)-5"-methyl-1"-heptyloxyphenyl]-2-(4-cyanophenyl)-pyrimidine.

EXAMPLE 3

Preparation of 5-[4'-(+)-2"-methyl-1"-butyloxyphenyl]-2-(4-cyanophenyl)-pyrimidine 2.0 G. of 5-[4'-(+)-2"-methyl-1"-butyloxyphenyl]-2-(4-bromophenyl)-pyrimidine are heated at reflux for 30 hours with 3.15 g. of copper-(I)cyanide in 100 ml. of dimethylformamide. The mixture is cooled, 50 ml. of 10% aqueous ethylenediamine solution are added thereto and the resulting mixture is stirred for a short period and then extracted with methylene chloride. The organic extract is again shaken with 30 ml. of ethylenediamine solution and then washed with water until neutral. The crude concentrate is chromatographed on silica gel with toluene/1% acetone. Recrystallization of the pure fractions from methanol/methylene chloride gives 5-[4'-(+)-2"-methyl-1"-butyloxyphenyl]-2-(4-cyanophenyl)-pyrimidine, having a melting point of 149.5° C. and clearing point of 233.5° C.

The starting material can be prepared as follows:

2.4 G. of p-bromobenzamidine hydrochloride, obtained from p-bromobenzonitrile in the usual manner, are added to a solution of 0.7 g. of sodium in 20 ml. of methanol and then treated (as described in Example 2) with 2.5 g. of crude 2-[4-(2-methylbutyloxy)phenyl]-3-ethoxyacrolein. The mixture is heated overnight at reflux, the solvent is subsequently distilled off partially and the residue is treated with ether. After acidification with dilute hydrochloric acid, the precipitate obtained is filtered off, washed thoroughly with water and ether and finally dried. The crude 5-[4'-(+)-2"-methyl-1"-butyloxyphenyl]-2-(4-bromophenyl)-pyrimidine is used in the process without further purification.

The following optically active pyrimidine derivatives can be prepared in an analogous manner:

5-[4'-(+)-2"-methyl-1"-butylphenyl]-2-(4-cyanophenyl)-pyrimidine, mp. 105.6°, cp. 206.7°,
5-[4'-(+)-3"-methyl-1"-pentylphenyl]-2-(4-cyanophenyl)-pyrimidine,
5-[4'-(+)-4"-methyl-1"-hexylphenyl]-2-(4-cyanophenyl)-pyrimidine,
5-[4'-(+)-5"-methyl-1"-heptylphenyl]-2-(4-cyanophenyl)-pyrimidine,
5-[4'-(+)-5"-methyl-1"-butyloxyphenyl]-2-(4-cyanophenyl)-pyrimidine, mp. 150.7°, cp. 233.8°,
5-[4'-(+)-3"-methyl-1"-pentyloxyphenyl]-2-(4-cyanophenyl)-pyrimidine, mp. 95.0°, cp 235.7°,
5-[4'-(+)-4"-methyl-1"-hexyloxyphenyl]-2-(4-cyanophenyl)-pyrimidine, having a melting point of 121°–122° C. and clearing point of 238.5° C.,
5-[4'-(+)-5"-methyl-1"-heptyloxyphenyl]-2-(4-cyanophenyl)-pyrimidine,
2-[4'-(+)-2"-methyl-1"-butylphenyl]-5-(4-cyanophenyl)-pyrimidine,
2-[4'-(+)-3"-methyl-1"-pentylphenyl]-5-(4-cyanophenyl)-pyrimidine,
2-[4'-(+)-4"-methyl-1"-hexylphenyl]-5-(4-cyanophenyl)-pyrimidine,
2-[4'-(+)-5"-methyl-1"-heptylphenyl]-5-(4-cyanophenyl)-pyrimidine,
2-[4'-(+)-2"-methyl-1"-butyloxyphenyl]-5-(4-cyanophenyl)-pyrimidine,
2-[4'-(+)-3"-methyl-1"-pentyloxyphenyl]-5-(4-cyanophenyl)-pyrimidine,
2-[4'-(+)-4"-methyl-1"-hexyloxyphenyl]-5-(4-cyanophenyl)-pyrimidine, and
2-[4'-(+)-5"-methyl-1"-heptyloxyphenyl]-5-(4-cyanophenyl)-pyrimidine.

The following Examples illustrate the preparation of the compounds of formula XI hereinbefore:

EXAMPLE A

Preparation of 2-(4-n-hexylphenyl)-5-(4-cyanophenyl)-pyrimidine 1.9 G. of 2-(4-n-hexylphenyl)-5-(4-bromophenyl)-pyrimidine are heated at reflux for 21 hours in 50 ml. of dimethylformamide with 2.5 g. of copper-(I) cyanide (content 70%). After cooling, the mixture is stirred with 25 ml. of 10% aqueous ethylenediamine solution and subsequently extracted with methylene chloride. The extract is again washed with aqueous ethylenediamine solution and then several times with water until neutral. The crude product obtained after evaporation is chromatographed on 150 g. of silica gel with toluene/1% acetone. There are obtained firstly traces of starting material and then fractions containing pure 2-(4-n-hexylphenyl)-5-(4-cyanophenyl)-pyrimidine. After recrystallization from acetic ester, the product has a melting point of 121.5° C. and a clearing point of 250° C.

The starting material can be obtained as follows:

A solution of 15 g. of 1-(4-bromophenyl)-2-methoxyethylene in 150 ml. of ethyl orthoformate is added dropwise at 0°–5° C. to 5 g. of boron trifluoride etherate in 200 ml. of ethyl orthoformate. The mixture is stirred overnight and reaches room temperature. The mixture is then diluted with ether and washed firstly with soda solution and then with water until neutral. The crude product obtained after evaporation yields 4-bromophenyl-malonic tetraacetal after recrystallization from hexane.

In order to partially hydrolyze the foregoing acetal, 4.5 g. thereof are dissolved in 10 ml. of ethanol, the solution is treated with 0.5 ml. of water and 1 drop of concentrated sulfuric acid and the mixture is stirred at 50° C. overnight and then worked-up in the usual manner. There is thus obtained crude 2-(4-bromophenyl)-3-ethoxyacrolein which is used in the crude form.

To a sodium methylate solution prepared from 0.7 g. of sodium in 25 ml. of methanol are added firstly 2.5 g. of crude 2-(4-bromophenyl)-3-ethoxyacrolein in 20 ml. of methanol and then 2.4 g. of 4-n-hexylbenzamidine hydrochloride. The mixture is heated to reflux overnight. Subsequently, the solvent is distilled off partially, the residue is treated with water and acidified with dilute hydrochloric acid. The resulting precipitate is filtered off, washed thoroughly with water and ether and dried. The crude 2-(4-n-hexylphenyl)-5-(4-bromophenyl)-pyrimidine, having a melting point of 152.5°–156° C., is used in the process without further purification.

The following compounds were prepared in an analogous manner:

|  | Melting Point | Clearing Point |
|---|---|---|
| 2-(4-Ethylphenyl)-5-(4-cyano-phenyl)-pyrimidine | 167°–167.5° C. | 279°–279.5° C. |
| 2-(4-n-Propylphenyl)-5-(4-cyanophenyl)-pyrimidine | 167° C. | 278.5°–279° C. |
| 2-(4-n-Butylphenyl)-5-(4-cyanophenyl)-pyrimidine | 138.5° C. | 266°–266.5° C. |
| 2-(4-n-Pentylphenyl)-5-(4-cyanophenyl)-pyrimidine | 131.5° C. | 262.5°–263° C. |
| 2-(4-n-Heptylphenyl)-5-(4-cyanophenyl)-pyrimidine | 121.5° C. | 245°–245.5° C. |

EXAMPLE B

Preparation of 5-n-pentyl-2-(4'-cyano-4-biphenylyl)-pyrimidine 1.5 G. of 5-n-pentyl-2-(4'-bromo-4-biphenylyl)-pyrimidine are heated at reflux for 22 hours with 2.5 g. of copper-(I) cyanide (content 70%) in 50 ml. of dimethylformamide. After cooling, 25 ml. of 10% aqueous ethylenediamine solution are added and, after stirring for a short time, the mixture is extracted with methylene chloride. The organic extract is shaken with a further 25 ml. of ethylenediamine solution and then washed until neutral. The crude concentrate is chromatographed on silica gel with toluene/1% acetone. Recrystallization of the pure fractions from ethyl acetate yields 5-n-pentyl-2-(4'-cyano-4-biphenylyl)-pyrimidine, having a melting point of 123.5°–124° C. and clearing point of 204.5°–205° C.

The starting material can be obtained as follows:

34.5 G. of 4-bromobiphenyl in 164 ml. of methylene chloride are treated at about 2° C. with 60.6 g. of titanium tetrachloride. At the same temperature there are added dropwise over a period of 40 minutes 20.7 g. of dichloromethyl methyl ether. The cooling means is removed and the mixture is left to stir at room temperature for 21 hours. The mixture is poured on to ice and the product is extracted with ether in the usual manner. Chromatography on silica gel using benzene for the elution gives firstly unreacted starting material and then 4'-bromo-4-biphenylaldehyde.

From 17.5 g. of 4'-bromo-4-biphenylaldehyde and 4.4 g. of hydroxylamine hydrochloride in 35 ml. of methanol and 70 ml. of pyridine there is obtained, after boiling under reflux, crude oxime, which is converted into the nitrile by heating for 15 hours in acetic anhydride. The mixture is concentrated as much as possible on a rotary evaporator. The residue is poured on to ice and dilute sodium hydroxide and the product is isolated with ether in the usual manner. After treatment with hexane, the 4'-bromo-4-cyanobiphenyl melts at about 150° C.

Gaseous hydrochloric acid is passed into a mixture of 5.6 g. of 4'-bromo-4-cyanobiphenyl and 1 g. of absolute ethanol in 25 ml. of toluene until the mixture becomes saturated. After stirring for 3 days at room temperature, the precipitate is filtered off and washed with toluene. The residue is suspended while still moist in 5 ml. of absolute ethanol and the suspension is treated with about 1.3 g. of ammonia in the form of a 10% ethanolic solution. After stirring for 3 days at room temperature, the precipitated 4'-bromo-4-biphenylamidine hydrochloride is separated, washed with ether and dried.

5.8 G. of n-pentyl-malonic tetraacetal are stirred at room temperature overnight in 10 ml. of ethanol with 0.75 ml. of water and 1 drop of concentrated sulfuric acid. The mixture is then diluted with ether, extracted with sodium carbonate solution, washed neutral and evaporated.

1.42 G. of the thus-obtained crude 2-n-pentyl-3-ethoxyacrolein are dissolved in a sodium ethylate solution (obtained from 580 mg. of sodium in 40 ml. of ethanol) and treated with 2.6 g. of the aforementioned 4'-bromo-4-biphenylamidine hydrochloride. The mixture is stirred at room temperature for 3 days. After some of the solvent has been distilled off, water is added and the mixture is extracted with chloroform in the usual manner. Upon crystallization from ethanol, there is obtained 5-n-pentyl-2-(4'-bromo-4-biphenylyl)-pyrimidine in the form of needles, having a melting point of 137° C. and a clearing point of 197° C.

The following compounds were obtained in an analogous manner:

5-n-Propyl-2-(4'-cyano-4-biphenylyl)-pyrimidine; melting point 125.6° C.; clearing point 275.7° C.;

5-n-butyl-2-(4'-cyano-4-biphenylyl)-pyrimidine; melting point 112° C; clearing point 262° C.;

5-n-hexyl-2-(4'-cyano-4-biphenylyl)-pyrimidine; melting point 108° C.; clearing point 245° C.; and 5-n-heptyl-2-(4'-cyano-4-biphenylyl)-pyrimidine; melting point 110° C.; clearing point 241.5° C.

We claim:

1. An optically active compound of the formula

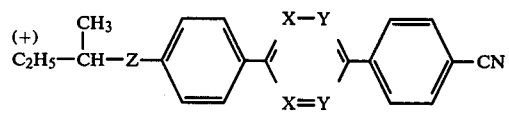

wherein Z is $-(CH_2)_n-$ or $-(CH_2)_n-O-$, wherein n is an integer of 1 to 4, and each of the symbols X is nitrogen and each of the symbols Y is $-CH-$, or each of the symbols Y is nitrogen and each of the symbols X is $-CH-$.

or its (−) optical antipode.

2. A compound in accordance with claim 1, 5-[4'-(+)-2''-methyl-1''-butylphenyl]-2-(4-cyanophenyl)-pyrimidine or its (−) optical antipode.

3. A compound in accordance with claim 1, 5-[4'-(+)-3''-methyl-1''-pentylphenyl]-2-(4-cyanophenyl)-pyrimidine or its (−) optical antipode.

4. A compound in accordance with claim 1, 5-[4'-(+)-4''-methyl-1''-hexylphenyl]-2-(4-cyanophenyl)-pyrimidine or its (−) optical antipode.

5. A compound in accordance with claim 1, 5-[4'-(+)-5''-methyl-1''-heptylphenyl]-2-(4-cyanophenyl)-pyrimidine or its (−) optical antipode.

6. A compound in accordance with claim 1, 5-[4'-(+)-2''-methyl-''-butyloxyphenyl]-2-(4-cyanophenyl)-pyrimidine or its (−) optical antipode.

7. A compound in accordance with claim 1, 5-[4'-(+)-3''-methyl-1''-pentyloxyphenyl]-2-(4-cyanophenyl)-pyrimidine or its (−) optical antipode.

8. A compound in accordance with claim 1, 5-[4'-(+)-4''-methyl-1''-hexyloxyphenyl]-2-(4-cyanophenyl)-pyrimidine or its (−) optical antipode.

9. A compound in accordance with claim 1, 5-[4'-(+)-5''-methyl-1''-heptyloxyphenyl]-2-(4-cyanophenyl)-pyrimidine or its (−) optical antipode.

10. A compound in accordance with claim 1, 2-[4'-(+)-2''-methyl-1''-butylphenyl]-5-(4-cyanophenyl)-pyrimidine or its (−) optical antipode.

11. A compound in accordance with claim 1, 2-[4'-(+)-3''-methyl-1''-pentylphenyl]-5-(4-cyanophenyl)-pyrimidine or its (−) optical antipode.

12. A compound in accordance with claim 1, 2-[4'-(+)-4''-methyl-1''-hexylphenyl]-5-(4-cyanophenyl)-pyrimidine or its (−) optical antipode.

13. A compound in accordance with claim 1, 2-[4'-(+)-5''-methyl-1''-heptylphenyl]-5-(4-cyanophenyl)-pyrimidine or its (−) optical antipode.

14. A compound in accordance with claim 1, 2-[4'-(+)-2''-methyl-1''-butyloxyphenyl]-5-(4-cyanophenyl)-pyrimidine or its (−) optical antipode.

15. A compound in accordance with claim 1, 2-[4'-(+)-3''-methyl-1''-pentyloxyphenyl]-5-(4-cyanophenyl)-pyrimidine or its (−) optical antipode.

16. A compound in accordance with claim 1, 2-[4'-(+)-4''-methyl-1''-hexyloxyphenyl]-5-(4-cyanophenyl)-pyrimidine or its (−) optical antipode.

17. A compound in accordance with claim 1, 2-[4'-(+)-5''-methyl-1''-heptyloxyphenyl]-5-(4-cyanophenyl)-pyrimidine or its (−) optical antipode.

* * * * *